(12) United States Patent
Sandlin et al.

(10) Patent No.: US 6,394,987 B1
(45) Date of Patent: May 28, 2002

(54) PORTABLE DISINFECTANT APPARATUS

(76) Inventors: Tamara Marie Sandlin, 2564 Robinwood, Toledo, OH (US) 43601; Matthew James Norris, 2405 Greenlawn, Toledo, OH (US) 43614

( * ) Notice: Subject to any disclaimer, the term of this patent is extended or adjusted under 35 U.S.C. 154(b) by 0 days.

(21) Appl. No.: 09/328,093

(22) Filed: Jun. 8, 1999

(51) Int. Cl.[7] .............................................. A61M 35/00
(52) U.S. Cl. ...................................... 604/289; 206/362
(58) Field of Search ................................ 604/289, 290, 604/310, 311, 403, 410, 415, 416, 191; 141/26, 27, 28; 366/101, 131, 137.1, 181.8, 182.2; 206/38.1, 221, 5.1, 438, 37, 533, 361, 362; 221/197, 198

(56) References Cited

U.S. PATENT DOCUMENTS

| | | | | |
|---|---|---|---|---|
| 4,171,753 A | * | 10/1979 | Vreede | ........................ 221/197 |
| 4,858,759 A | * | 8/1989 | Mauthe et al. | ............... 206/221 |
| 5,533,994 A | * | 7/1996 | Meyer | ........................ 604/416 |
| 5,551,849 A | * | 9/1996 | Christiansen | ............... 417/472 |
| 5,573,109 A | * | 11/1996 | Isacson | |
| 6,056,118 A | * | 5/2000 | Hargus et al. | ............... 206/438 |

* cited by examiner

*Primary Examiner*—Anhtuan T. Nguyen
*Assistant Examiner*—Ann Y Lam
(74) *Attorney, Agent, or Firm*—Benjamin A. Randall

(57) ABSTRACT

A device for holding and dispensing a disinfectant liquid such as isopropyl alcohol from one section of the device, and holding and dispensing sterile swabs from another section of the device. A single unit combines a storage and delivery unit for the liquid disinfectant and a storage and delivery unit for sterile swabs. The liquid disinfectant is stored in a refillable container with a pump for delivering the disinfectant. The disinfectant storage unit is refilled with a hollow needle, puncturing a self-sealing membrane and injecting the disinfectant fluid into the storage unit. Complete sterility of the disinfectant fluid can thereby be maintained. A second holding and dispensing unit is combined with the liquid unit. A series of individually wrapped sterile swabs is stacked into a spring-loaded cylinder. Swabs are individually removed from one end of the unit, and replaced by the next one in the stack. The device allows a health care professional to always have available the equipment needed for dermal sterilization, and minimizes waste normally associated with these supplies. Alternatively, the swabs may be stored in the cylinder separated by an impervious barrier, allowing the swab to be used while held and contained by the cylinder.

12 Claims, 7 Drawing Sheets

PORTABLE DISINFECTANT APPARATUS

BACKGROUND OF THE INVENTION

1. Field of the Invention

This invention relates in general to devices for dispensing liquids and solids. Specifically, this device is a portable isopropyl alcohol storage and dispensing unit in combination with a sterile swab storage and dispensing unit. This device is worn around the neck of the user, dipped to an article of clothing, or carried.

2. Description of the Related Art

The injection of fluids into the human body using hypodermic needles requires that the dermal region to be punctured be disinfected or sterilized. The current state of art in health care environments is to use an individually wrapped disposable swab &hat is usually pre-saturated with a disinfectant liquid such as isopropyl alcohol. To prevent cross contamination of patients, the swab used for the disinfectant process must be discarded after a single use. Environments where numerous injections are given on a daily basis such as a hospital, require that a large number of swabs and a large quantity of disinfectant always be on hand. Typically, swabs are individually wrapped in packaging that can be as voluminous as the swab itself, creating a high degree of packaging waste. Further, the person administering the injection will have to carry a large number of swabs around with them or arrange to have them stored in or near every hospital room. The same conditions govern the disinfectant supply which being liquid is even more difficult to transport. A further disadvantage of the existing art is that the swabs have a tendency to dry out fairly quickly due to the volatility of the sterilizing fluid, at times therefore requiring the use of more than one swab on a single patient. A fair sized hospital will use hundreds of swabs on a typical day, generating a large amount of waste, and a large expense. The present invention addresses these problems by providing sterile dry swabs and a user controlled amount of disinfectant fluid that is applied at the point of use, embodied as a single, portable unit.

SUMMARY OF THE INVENTION

This invention relates generally to devices for dispensing liquids and solids, and more specifically to a portable device for holding and dispensing a disinfectant liquid such as isopropyl alcohol from one section of the device, and holding and dispensing sterile swabs from a separate section of the device. The present invention provides a solution to the problems of storage, availability, and waste associated with the normal method of dermal disinfecting. The present invention is a unitary device that combines a storage and delivery unit for the liquid disinfectant, and a storage and delivery unit for sterile swabs. The device can be worn about the neck or clipped to an article of clothing. The liquid disinfectant is stored in a refillable container with a pump for delivering the disinfectant. A self-sealing membrane such as the type that is used on vials for delivery of injectable medications is provided for refilling the liquid storage unit using a hypodermic needle.

The swabs are stored in a spring-loaded cylinder that provides for individual delivery of the swabs, and allows them to be stored in a closed environment. Since only the swab to be immediately used is touched, the sterility of swabs is not compromised, and there is no need to individually wrap the swabs. The sterile cotton swabs may be stored in the unit such that there is no packaging separating them or a thin film of material to enhance removal may separate them. In either method, the necessary packaging is minimized.

An alternative embodiment of the invention contemplates using the portable disinfectant apparatus as a holder for the sterile swabs. A surface of the sterile swab would protrude from the apparatus, and the apparatus could be used much like a marking pen, the protruding surface of the sterile swab available to scrub the dermal region desired to be disinfected, the disinfectant apparatus supporting and holding the body of the sterile swab. The sterile swabs stored in the unit in this embodiment would be separated by sufficient solvent impervious material to prevent contamination of the unexposed swabs.

This invention therefore provides an apparatus for conveniently storing and dispensing a disinfectant liquid and sterile swabs. It also provides an apparats which minimizes the waste normally associated with the hospital disinfectant process, by supplying a refillable liquid storage and dispensing unit combined with a unit for dispensing sterile swabs that accommodates minimal packaging while maintaining sterility. This invention further provides a portable supply of swabs and liquid disinfectant that can be conveniently carried, worn about the neck, or clipped to an article of clothing.

DESCRIPTION OF PREFERRED EMBODIMENT

Figure 1:
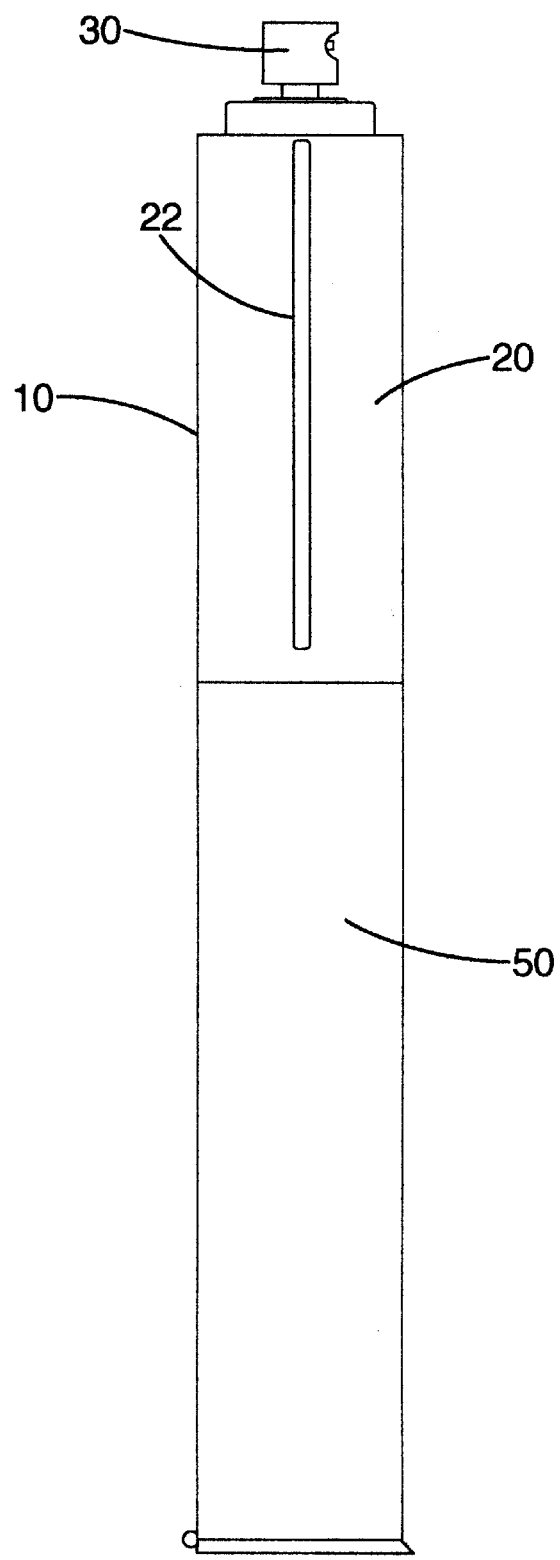
FIG. 1 is an isometric view of the portable disinfectant apparatus.
Figure 2:
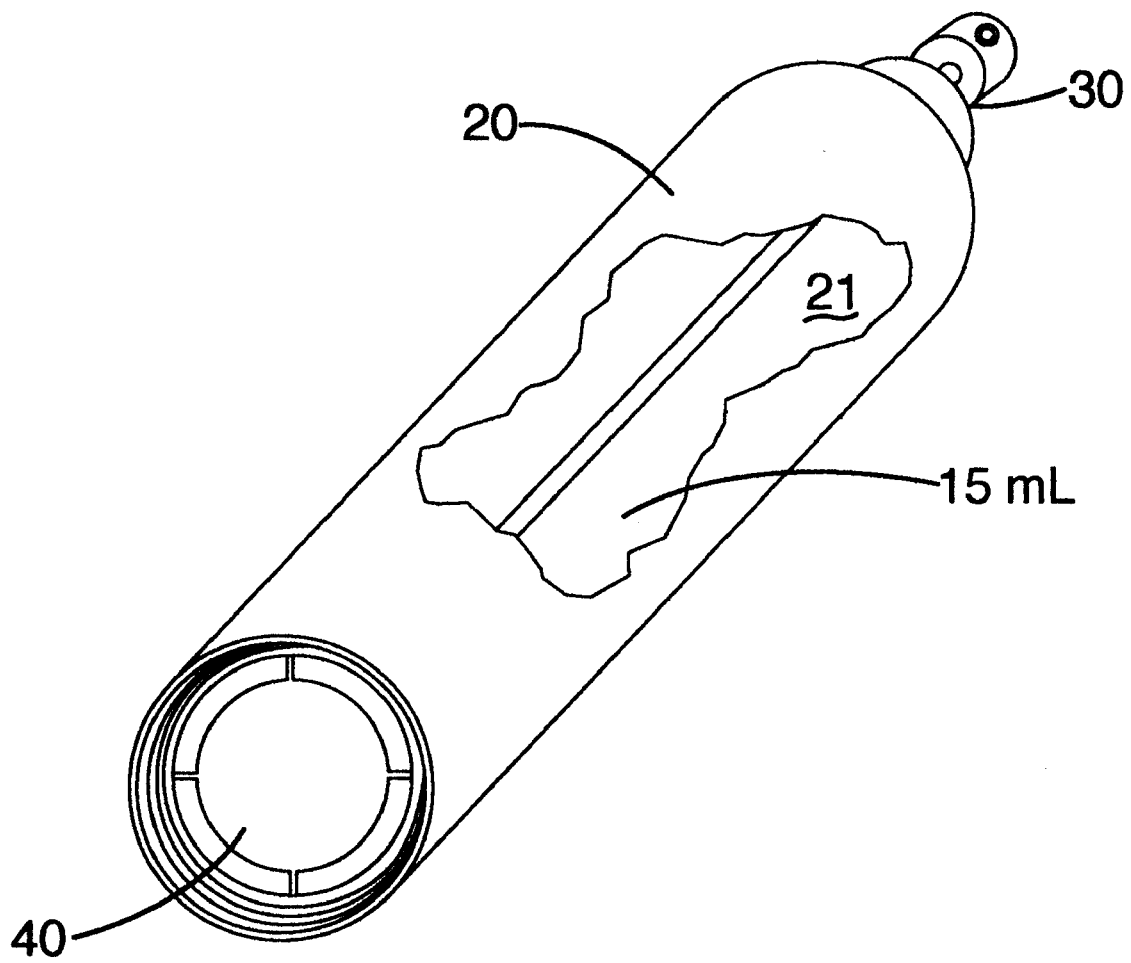
FIG. 2 is a breakaway view of the liquid storage and dispensing unit showing the pump and the self-sealing membrane.

Referring to FIG. 1, the portable disinfectant device is shown generally at 10. The portable disinfectant device 10 includes a liquid storage unit 20, and a swab storage unit 50. Referring to FIG. 2, the liquid storage unit 20 consists of a cylindrical liquid storage space 21 with a delivery pump assembly 30 at one end, and a self-sealing membrane assembly 40 at the opposite end. The liquid storage unit 20 is made of a moldable plastic material that is resistant to the solvent effects of sterilizing fluids such as isopropyl alcohol. In a first embodiment of the invention, the liquid storage unit 20 and the swab storage unit 30 are made from PVC plastic, but other injectable or moldable polymeric materials can be used.

Figure 3:
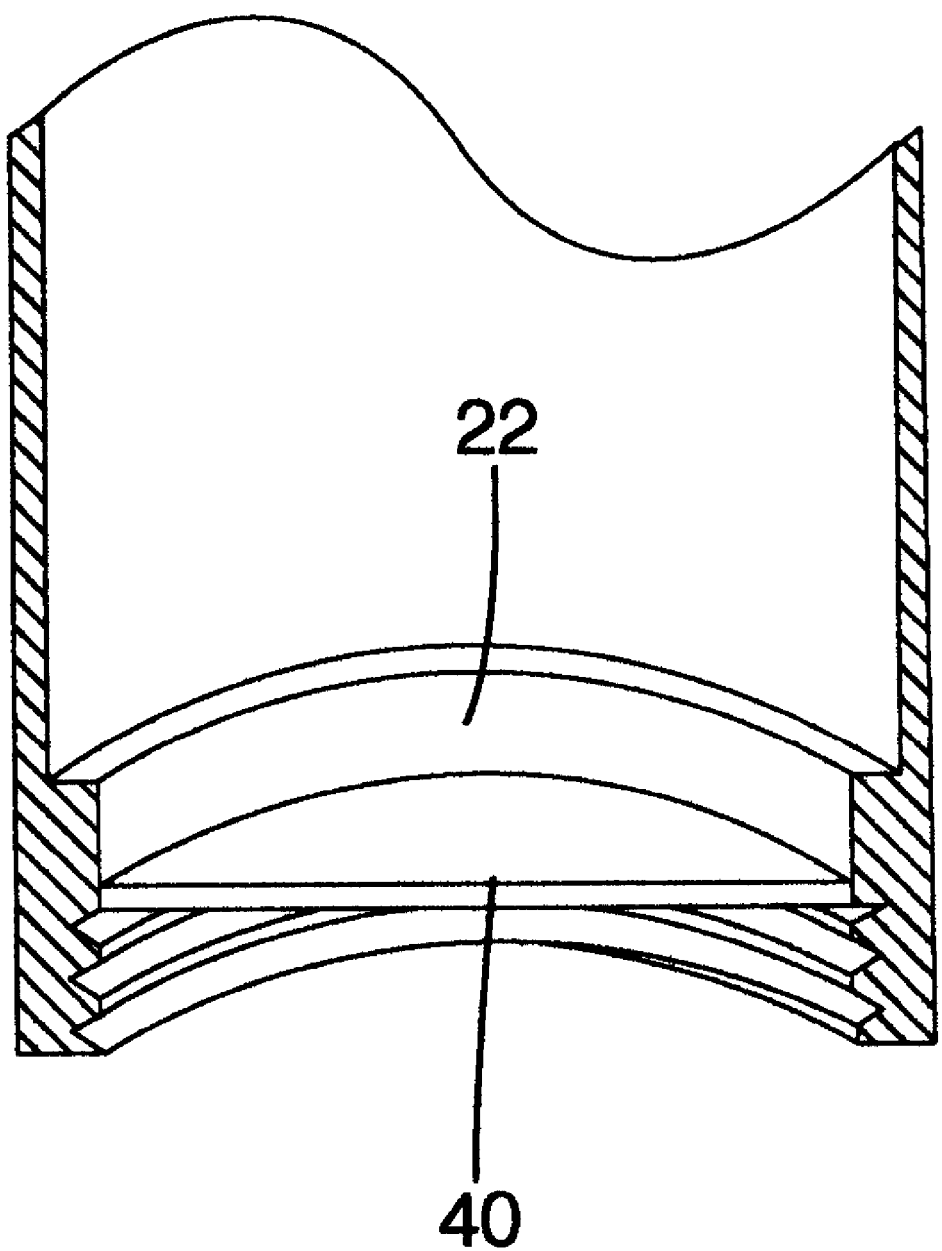
FIG. 3 is a detail view of the self-sealing membrane as attached to the liquid storage unit.
Figure 4:
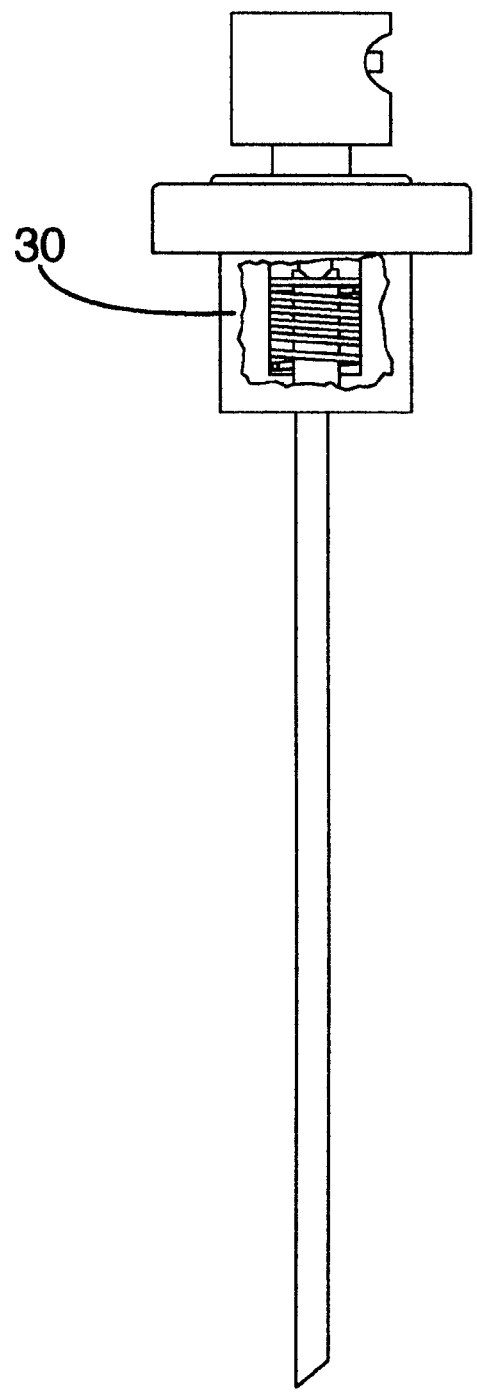
FIG. 4 is a detail drawing of the pump assembly.

Referring to FIGS. 2, 3, and 4, the liquid storage unit 20 is a hollow cylindrical structure sealed at one end by the pump assembly 30 and at the other end by the self-sealing membrane 40. The inner wall of the liquid storage unit 20, the pump assembly 30, and the self-sealing membrane 40 defines the liquid storage space 21. In a first embodiment of the invention, the pump assembly 30 is secured to the liquid storage unit 20 using a threaded connection. It is anticipated that the pump assembly 30 could eventually fail due to repeated cycling, and the threaded assembly method will allow for replacement of the pump assembly 30. In alternate embodiments of the invention, the pump assembly 30 may be permanently attached to the liquid storage unit 20 by means of autogenous bonding achieved by the application of infrared, ultrasonic or radio frequency (RF) energy or gluing with any suitable solvent impervious adhesive.

Referring to FIG. 3, on the end of the liquid storage unit 20 opposite the pump assembly 30, the self-sealing membrane 40 is attached to the liquid storage unit 20. The liquid storage unit 20 is formed such that there is a concentric land area or retaining lip 22 extending inward from the interior wall of the liquid storage unit 20. The self-sealing membrane 40 is permanently attached to the retaining lip 20 also by means of autogenous bonding. The self-sealing membrane 40 may also be attached to the liquid storage unit 20 by means of mechanical attachment mechanisms such as mounting the self-sealing membrane 40 on a threaded ring and providing complementary threads on an interior of the liquid storage unit 20, or by using a snap ring with a complementary retaining groove in an interior wall of the liquid storage unit 20, or by integrating a metallic ring into the body of the liquid storage unit 20, and then crimping it over the self-sealing membrane 40 after installation. Any mechanical attachment of the self-sealing membrane 40 should have means for providing a leak tight seal, such as an o-ring or gasket.

An alternate embodiment of the invention does not have the self-sealing membrane 40 located at the end of the liquid storage unit 20 opposite the pump assembly 30, but incorporates the self-sealing membrane into the side wall of the liquid storage unit 20. The self-sealing membrane 40 is of the type typically used in dispensing liquid medications with a hypodermic needle. The self-sealing membrane 40 may be of any thickness that can accommodate repetitive piercing without failure. In particular, when the self-sealing membrane is located on an end of the liquid storage unit 20, it will be generally disc shaped. The self-sealing membrane 40, when incorporated in the sidewall of the liquid storage unit 20 will be plug shaped.

Referring to FIG. 1, incorporated into the wall of the liquid storage unit 20, is a transparent window 22 that allows visual observation of the contents of the liquid storage space 21. The window 22 can be made from any suitable material that exhibits resistance to the solvent effects of the disinfectant liquid, and that can be easily incorporated into the forming process of the liquid storage unit 20, or may be easily incorporated thereafter. In a first embodiment of the invention, the window 22 is made from a clear plastic. In all further embodiments, the window 22 is made from glass or clear acrylic or polymeric material. In a first embodiment of the invention, the window 22 is autogenously bonded into an opening left when the liquid storage unit is made. In further embodiments, the window 22 may be integrally formed as part of the molding process. The size of the window 22 is such that sufficient light enters the interior of the liquid storage space 21 to enable visual inspection of the contents. In a first embodiment, the window 22 extends the length of the liquid storage space 22, and is approximately ⅛" wide. In other embodiments, the window may be of any size shape or location that enables inspection of the contents of the liquid storage space 22.

Referring again to FIG. 1, the liquid storage unit 20 can be seen attached to the swab storage unit 50. The swab storage unit 50 is removably attached to the liquid storage unit 20 so that the self-sealing membrane 40 may be accessed for refilling by removing the swab storage unit 50. The self-sealing membrane 40 is protected from contamination and from accidental puncturing when the swab storage unit 50 is reattached.

Figure 5:
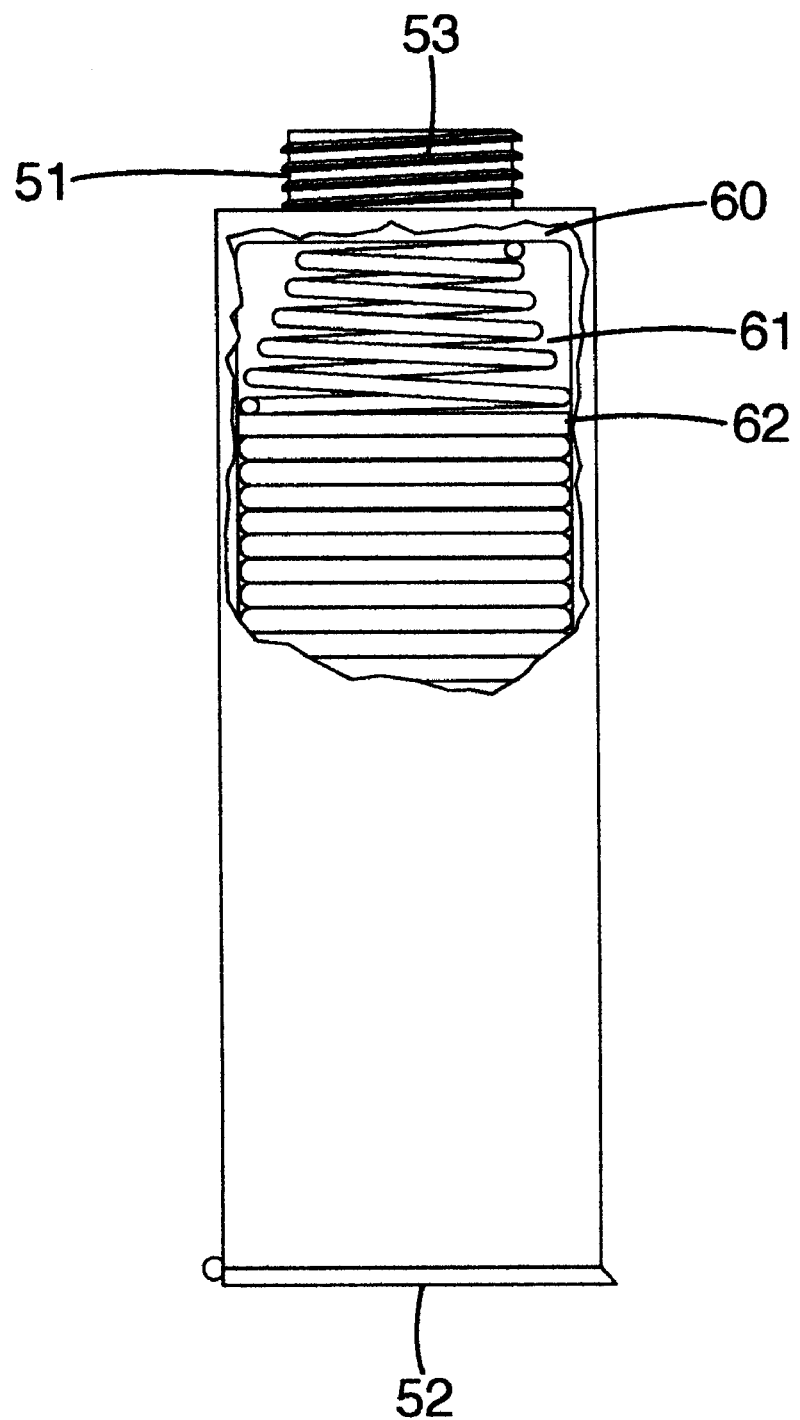
FIG. 5 is a detail drawing of the swab storage unit showing the pressure plate and spring.

Referring to FIG. 5, the swab storage unit 50 is an elongated cylindrical structure of similar diameter to the liquid storage unit 20, having an attachment end 51, and a dispensing end 52. The attachment end 51 includes a threaded portion 53 which mates with a complementary threaded portion on the liquid storage unit 20 at the end opposite the pump assembly 30. In a first embodiment of the invention, the swab storage unit 50 is removably attached to the liquid storage unit 20 using complementary threaded areas. In further embodiments, the swab storage unit 50 may be removably attached to the liquid storage unit 20 by mechanical attachment means such as mating tabs and slots including the twist-and-lock type, a press-fit ridge and valley arrangement, or a spring-loaded ball and depression. The swab storage unit 50 may also be permanently attached to the liquid storage unit 20, in those embodiments of the invention that incorporate the self-sealing membrane into the sidewall of the liquid storage unit 20.

Referring to again to FIG. 5, a support disc 60, a conical spring 61 and a pressure plate 62, used to force the dry sterile swabs from the swab delivery unit 50, may be seen. Dry sterile swabs are placed in a stack in the interior space of the swab storage unit 50. The swab storage unit 50 includes the support disc 60 located near the end of the swab storage unit 50 attached to the liquid storage unit 20. The support disc 60 is an integral part of the swab storage unit 50, which closes off the end of the swab storage unit 50, forming thereby in conjunction with the interior wall of the swab storage unit 50, an elongated cylindrical well being closed at the attachment end 51. The support disc 60 serves as a foundation and base for the conical spring 61, which in turn supports and applied pressure to the pressure plate 62. The pressure plate 62 supports a stack of sterile swabs, which are placed into the interior of the swab-dispensing unit 50. The conical spring 61 is sized so that it will extend the entire length of the interior space of the swab storage unit 50, and apply sufficient pressure to the pressure plate 62 to enable pressure to be applied to the stack of sterile swabs the entire length of the interior space of the swab storage unit 50. A first embodiment of the invention uses a conical spring to supply the necessary pressure for delivery of the sterile swabs, but further embodiments may use linear springs incorporated into the side wall of the swab storage unit, or may use a linear spring directly beneath the pressure plate 62. Using a conical spring for supplying the pressure allows the maximum amount of travel of the pressure plate 62, since conical springs can collapse into essentially one wire diameter thickness. A different spring type may be used with the invention if it is desired to use a different or thicker type of swab that may require a different delivery pressure. Swabs that are individually wrapped may require a stronger spring due to friction reaction with the interior wall of the swab dispensing unit 50. The pressure plate 60 may be flat, or may assume a convex shape. A convex shape would assist in removing the sterile swabs from the swab dispensing unit 50, by forcing the middle area of the swab to protrude from the dispensing end 52. In an embodiment of the invention where the swabs are retained within the dispensing unit while used, a convex pressure plate will assist in the disinfecting process also by causing a surface of a swab to protrude. Alternative embodiments of the invention encompass swabs that are of non-uniform thickness, achieving the same result. Swabs that are thicker in the middle than the periphery will also assist in the disinfecting process. The conical spring 62 may be attached to either or both the support disc 60 and the pressure plate 62 by any suitable attachment means such as adhesive or mechanical devices, or it may ride freely within the storage space.

Figure 6:
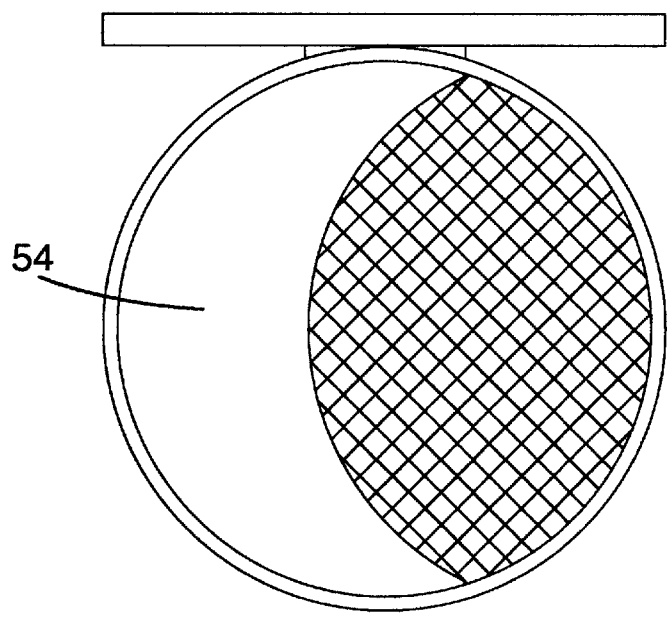
FIG. 6 is a detail drawing of the swab-dispensing end showing the retaining lip.
Figure 8:
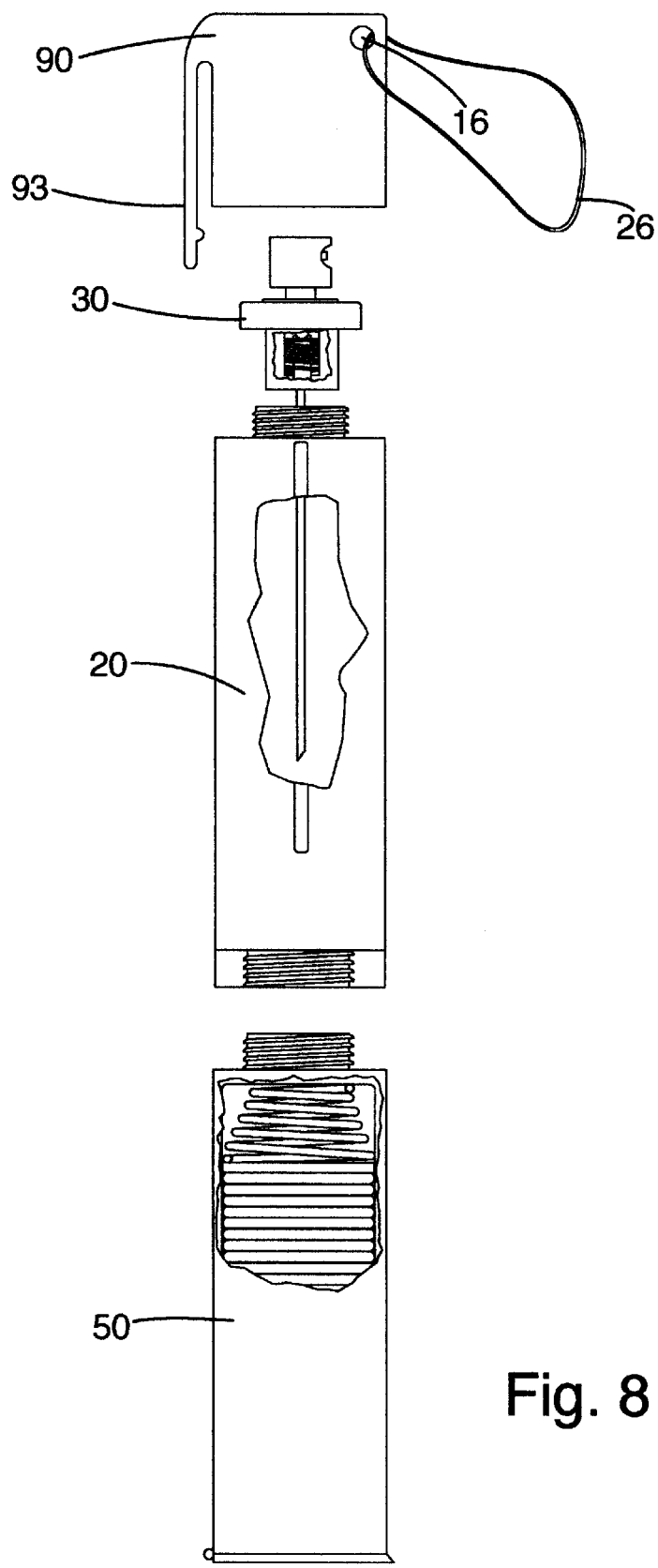
FIG. 8 is a breakaway drawing of the entire invention, showing the relationship between the subassemblies, and further showing a cover placed over the pump assembly.

Referring to FIGS. 5 and 6, the dispensing end 52 of the swab dispensing unit 50 is generally open, including a retaining lip 54, and a hinged lid 55. The retaining lip 54 is attached to the dispensing end 52 of the swab dispensing unit 50, and extends in an inwardly direction, generally perpendicular to the wall of the swab storage unit 50. The retaining lip 54 extends far enough over the open dispensing end 52 to prevent the unintended release of sterile swabs due to the pressure supplied by the conical spring 61 and the pressure plate 62, but allows sufficient room to allow an operator to grasp and remove a swab. In a first embodiment of the invention, the retaining lip 54 is a shallow U-shape, allowing the swabs to be removed from the top of the U. In further embodiments the retaining lip may be any shape that has sufficient surface area to prevent spontaneous release of the sterile swabs but allows the operator to easily remove them, such as a continuous circular or elliptical lip. Such a shape is also envisioned for use in the embodiment where the swabs are retained in the apparatus during the disinfecting process. The retaining lip 54 may be permanently attached to the body of the swab-dispensing unit 50, or may be removable. If the retaining lip 54 is permanently attached, sufficient opening must remain to accommodate insertion of the replacement sterile swabs. In the first embodiment of the invention, the retaining lip 54 is separately formed and then permanently attached to the body of the swab dispensing unit 50 after the conical spring 61 and the pressure plate 62 are placed in the interior space of the swab dispensing unit 50. The retaining lip 54 is then permanently attached to the body of the swab-dispensing unit 50, using any suitable adhesive, or using an autogenous bonding process. In further embodiments, the retaining lip 54 is removably attached to the swab-dispensing unit using threaded or other mechanical attachment means. In the embodiments where the retaining lip 54 is removably attached, the conical spring 61 will be attached to the support disc 60, and the pressure plate 62, to prevent them from falling out when the swab dispensing unit 50 is refilled.

Figure 7:
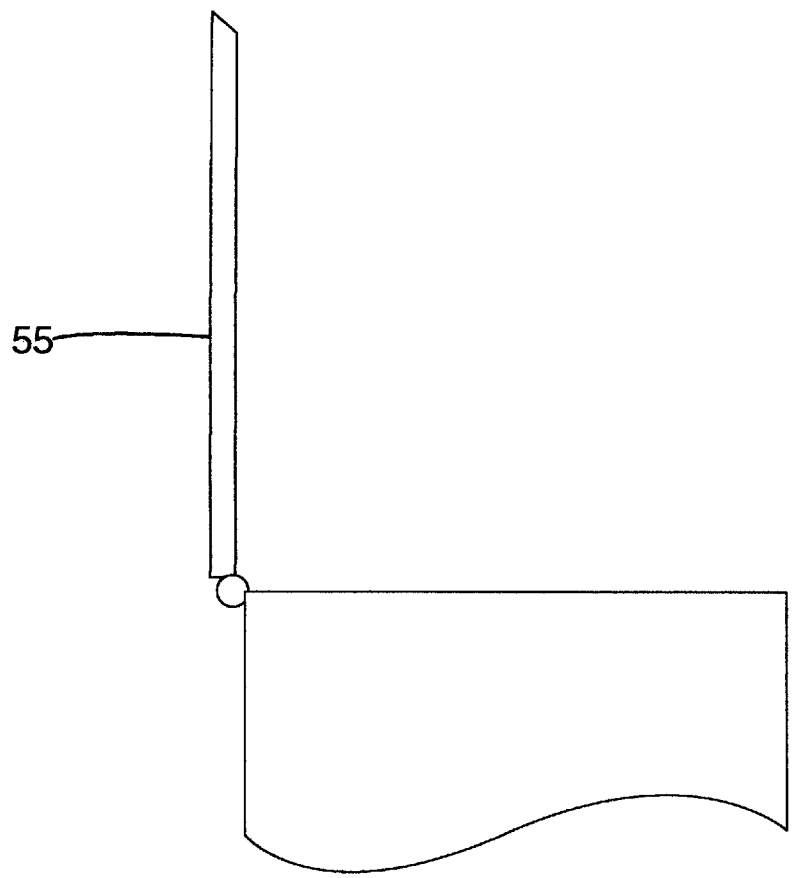
FIG. 7 is a detail drawing of the swab dispensing unit end showing a hinged cover.

The sterile swabs are protected from contamination by the hinged lid 55. The hinged lid 55 is attached to the dispensing end 52 of the swab storage unit 50, and in a first embodiment of the invention, will be hinged on one side, so the hinged lid 55 can flip up and allow access to the sterile swabs. Referring to FIG. 7, a hinge 56 will be integrated into the body of the swab storage unit 50, and will consist of a pin and block arrangement as is well known in the art. In further embodiments, the hinged lid 55 may be completely removable and be attached to the swab dispensing unit 50 by a tether, or may be threadably attached, or may snap on.

We claim:

1. A device for disinfecting a dermal region comprising in combination:
    a refillable liquid storage and dispensing unit for holding a disinfectant, said liquid storage and dispensing unit having an open first end, a sealed second end and a hollow body disposed therebetween,
    a pump spray assembly releasably secured to said open first end of said liquid storage and dispensing unit thereby forming an enclosed interior space, and in fluid communication with said liquid storage and dispensing unit for dispensing the disinfectant, wherein said second sealed end comprises a self-sealing membrane secured to said hollow body, an interior face of said membrane in communication with said interior space and an exterior face of said membrane in communication with the atmosphere,
    a swab storage and dispensing unit having a first end, a second end and a hollow body disposed therebetween wherein said first end of said swab storage and dispensing unit is releasably secured to said second sealed end of said liquid storage and dispensing unit and said second sealed end of said liquid storage and dispensing unit prevents fluid communication of the disinfectant from said liquid storage and dispensing unit to said swab storage and dispensing unit,
    a spring mechanism located within said hollow body of said swab storage and dispensing unit, said spring mechanism comprising a spring with a first end and a second end, said first end of said spring abutted and affixed to an interior face of said closed first end of said swab storage and dispensing unit, said second end of said spring affixed to a first face of a planar pressure plate having a nominal thickness and two opposite and generally parallel faces.

2. The device as recited in claim 1 wherein said sealed second end of said liquid storage and dispensing unit comprises a self-sealing penetrable membrane secured to said hollow body at a periphery of said membrane, an interior face of said membrane in communication with said interior space of said hollow body, and an exterior face of said membrane in communication with the atmosphere.

3. The device as recited in claim 2 wherein said sealed second end of said liquid storage and dispensing unit further comprised a hollow cylindrical threaded coupling having external threads and an interior surface, said coupling aligned with a longitudinal axis of said hollow body.

4. The device as recited in claim 3 wherein said swab storage and dispensing unit further comprises a female threaded portion at said first end of said swab storage and dispensing unit.

5. The device as recited in claim 3 wherein said self sealing penetrable membrane is affixed at said periphery to said interior surface of said threaded coupling.

6. The device as recited in claim 1 wherein said second end of said swab storage and dispensing unit is generally open, comprising a lip extending inward and partially covering said second end of said swab storage and dispensing unit.

7. The device as recited in claim 6 wherein a plurality of swabs is contained within said hollow body of said swab storage and dispensing unit.

8. The device as recited in claim 7 wherein said second face of said pressure plate is in contact with and urging said swabs toward said lip.

9. The device as recited in claim 7 wherein a cover is hingedly attached to said open second end of said swab storage and dispensing unit.

10. The device as recited in claim 1 wherein said pump spray assembly comprises a manually actuated displacement spray pump in fluid communication with said liquid storage and dispensing unit.

11. The device as recited in claim 1 further comprising a cap releasably secured to an outside surface of said liquid storage and dispensing unit, said cap covering said pump spray assembly.

12. The device as recited in claim 11 wherein said cap includes an eye for securing a lanyard.

* * * * *